United States Patent [19]

Mano et al.

[11] Patent Number: 4,904,601
[45] Date of Patent: Feb. 27, 1990

[54] CELL CULTURE TANK

[75] Inventors: Takashi Mano, Ishibashi; Akihiko Murakami, Ekihigashi; Masatsugu Ueda, Kawagoe; Eitaro Kumazawa, Oyama, all of Japan

[73] Assignee: Snow Brand Milk Products Co., Ltd., Japan

[21] Appl. No.: 309,567

[22] Filed: Feb. 13, 1989

[30] Foreign Application Priority Data

Feb. 16, 1988 [JP] Japan .................................. 63-33663

[51] Int. Cl.⁴ ............................................. B01F 3/04
[52] U.S. Cl. ..................................... 435/314; 435/315
[58] Field of Search ............................... 435/314–316, 435/818

[56] References Cited

U.S. PATENT DOCUMENTS

| 4,256,839 | 3/1981 | Solomons et al. | 435/314 |
| 4,814,278 | 3/1989 | Hamamoto et al. | 435/315 |
| 4,847,203 | 7/1989 | Smart | 435/314 |

FOREIGN PATENT DOCUMENTS 99634 2/1984 European Pat. Off. ............. 435/314
236111 5/1986 U.S.S.R. .............................. 435/315

Primary Examiner—James C. Yeung
Attorney, Agent, or Firm—Griffin, Branigan & Butler

[57] ABSTRACT

Here is disclosed a cell culture tank comprising a cylindrical screen mounted upright within the cell culture tank and having upper and lower openings through which culture medium flows, a pipe for supply of oxygen or oxygen containing gas and an agitator adapted to produce a flow of the culture medium, both the pipe and the agitator being provided within the cylindrical screen, wherein the agitator drives the culture medium to flow downward through the lower opening of the cylindrical screen, then to flow upward into a space defined between the cylindrical screen and the inner wall of the cell culture tank, and a relationship between an ascending velocity of the culture medium and a sinking velocity of the adherent carriers produces in the space between the cylindrical screen and the inner wall of the cell culture tank a floating region within which the adherent carriers float in the culture medium and a separating region within which the adherent carriers are separated from the culture medium.

8 Claims, 7 Drawing Sheets

CELL CULTURE TANK

BACKGROUND OF THE INVENTION

The present invention relates to a cell culture tank for culture and growth of target cells utilizing adherent cells requiring adherent carriers.

Mass cell culture is a technique essential to the industrial production of the biological medicines, for example, anti-viral drug such as virus, vaccine and interferon, or hormones. Particularly, production of monoclonal antibody for the purpose of producing specific proteins had been impossible in practice until mass culture of hybridoma cells has recently been achieved by hybridization of antibody producing cell and myeloma cell.

The cell culture using adherent cell which requires adherent carrier has conventionally depended on various techniques such as those utilizing roller bottle, multiplate and microcarrier. Among them, the typical technique of mass culture has been the microcarrier method in which the cell culture is performed with the microcarriers floating in culture medium.

However, the microcarrier method of the prior art has been disadvantageous in that the oxygen supply is too limited to maintain a high density cell culture, since the oxygen supply depends on the surface area in such microcarrier method of the prior art.

To overcome such problems, various solutions have been disclosed, for example, in Japanese Patent Disclosure No. 1987-122581, in accordance with which oxygen or oxygen containing gas is supplied from the bottom of the culture tank directly into the culture medium. However, such direct supply of oxygen or oxygen containing gas into the culture medium in which the adherent carriers carrying the cells adhering thereto float has often raised problems that an intense turbulent flow is developed in the culture medium and the cells are damaged by a shearing force of this turbulent flow and that the adherent carriers are driven upward by air bubbles, then adhere to the inner wall of the culture tank at the upper part thereof and the associated means such as sensors, and finally cease to float, interfering with the desired culture.

Figure 6:
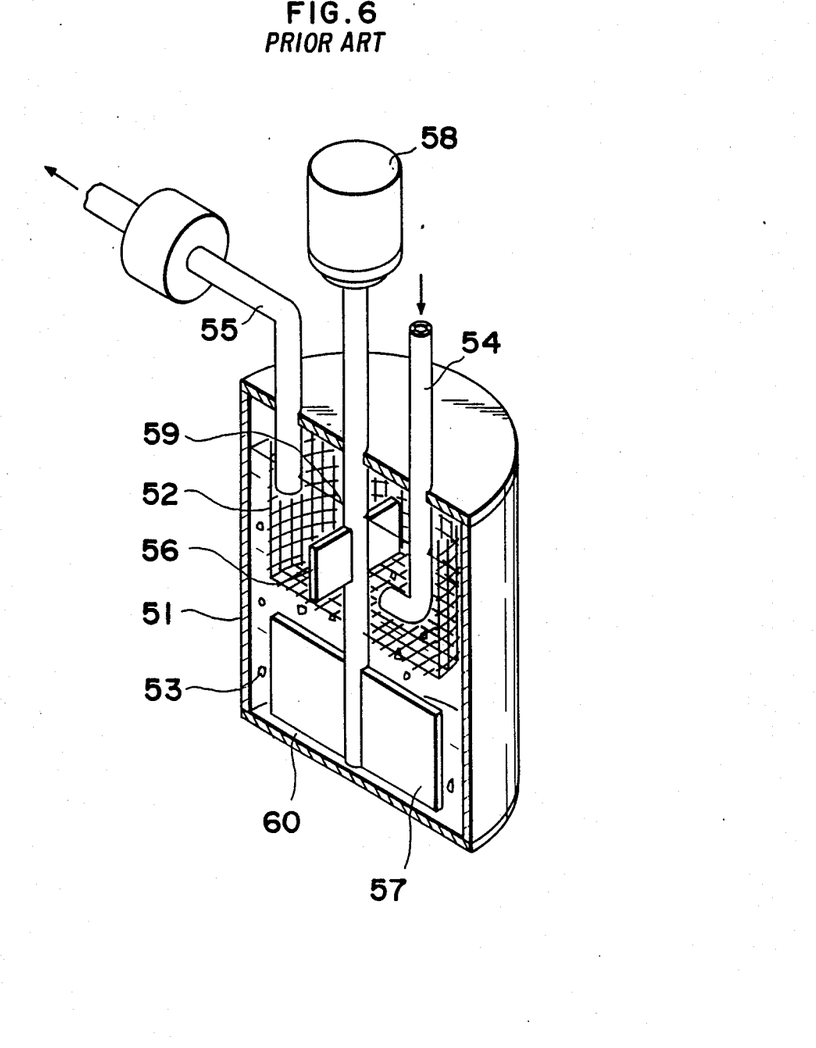
FIG. 6 is a perspective view showing the cell culture tank disclosed in Japanese Patent Application No. 1987-336366 of the inventors

In view of these problems, the inventors proposed the solution in Japanese Patent Application No. 1987-336366, of which the representative embodiment is shown by FIG. 6 of the accompanying drawing. Referring to FIG. 6, there is provided within a culture tank 51 a cylindrical filter 52 adapted to pass culture medium therethrough but to block adherent carriers 53 with cells adhering thereto. A region 59 surrounded by said filter 52 is filled only with the culture medium and none of the adherent carriers 53 floating therein within this region 59. The culture medium is supplied or drawn off through a conduit 55. Reference numeral 54 designates a conduit used to supply oxygen or air into the region 59. Agitator vanes 56, 57 are driven by an electromotor 58 and serve to agitate the culture medium within the regions 59, 60, respectively.

According to this prior invention of the inventors, the supply of oxygen or air is made only to the region 59 isolated by the filter 52 so that the cells floating outside this region 59 are free from any mechanical damage by a shearing force developed due to turbulent flow and the quantity of culture medium adequately supplied with oxygen in this region 59 permeates through the entire side wall of the filter 52 into the culture medium outside said region 59. Such arrangement enables not only a high density cell culture to be easily achieved but also continuous culture to be maintained for a long period.

However, even such improvement remains disadvantageous in that the agitator vane 57 provided in the region 60 causes a shearing force which may directly damage the cells floating therein.

SUMMARY OF THE INVENTION

It is the object of the present invention to provide a cell culture tank for a high density cell culture so improved as to supply culture medium with an adequate quantity of oxygen to be consumed by cells without any mechanical damage to these cells.

The object as set forth just above is achieved, in accordance with the present invention, by a cell culture tank comprising a cylindrical screen mounted upright within a cell culture tank and having upper and lower openings through which culture medium flows, a pipe for supply of oxygen or oxygen containing gas and an agitator adapted to produce a flow of the culture medium, both said pipe and said agitator being provided within said cylindrical screen, so that a space defined between the cylindrical screen and the inner wall of the cell culture tank vertically consists of a floating region within which adherent carriers float in the culture medium and a separating region within which said adherent carriers are separated from the culture medium.

As an alternative arrangement of the present invention, it is contemplated that there are provided a filter extending in the upper opening of the cylindrical screen and between said cylindrical screen and the inner wall of the cell culture tank so as to pass the culture medium therethrough but to block the adherent carriers, and vibration or rotation means to avoid a possible filter clogging.

It is also possible within a scope of the invention to connect the cylindrical screen with the agitator so that the cylindrical screen also may be rotated together with the agitator and thereby develop a rotating flow of the culture medium.

Now a manner in which the cell culture tank of this invention operates will be discussed.

According to the present invention, the supply of oxygen or oxygen containing gas into the culture medium is made within the region isolated by the cylindrical screen and the quantity of culture medium thus supplied with oxygen or oxygen containing gas flows downward under action of the agitator through the lower opening of the cylindrical screen and then upwardly into the region defined by the cylindrical screen and the inner wall of the cell culture tank.

During this upward flowing, the adherent carriers are separated from the culture medium and only the culture medium flows through the upper opening of the cylindrical screen into the latter.

Then, an effect provided by the present invention will be considered.

Within the cylindrical screen, both the supply of oxygen or oxygen containing gas and the presence of the agitator vane cause no mechanical damage to the cells, because the quantity of culture medium contains none of the adherent carriers. This enables a large quantity of oxygen consumed by the cells to be supplied into the culture medium and thereby facilitates the high density cell culture. Thus, use of circulating means permits a continuous culture to be maintained for a long period.

Upward flow of the culture medium is effectively agitated only by flowing of the culture medium itself and thereby avoid development of a shearing force directly exerted on the cells which would occur when a direct mechanical agitation is employed.

According to the present invention, the cell culture can be achieved within the culture tank which is extremely simplified but provided with the unique filter permitting the flow of culture medium to be accelerated to the maximum. In addition, the culture medium agitator provided within the cylindrical screen is controllable to accommodate a wide variation of the culture condition. Further, suitable means to avoid filter clogging may be provided to maintain continuous culture for a long period.

BRIEF DESCRIPTION OF THE DRAWING

These and other objects as well as advantages of the present invention will become clear by the following description of preferred embodiments of the present invention with reference to the accompanying drawings, wherein.

DESCRIPTION OF THE INVENTION

(Embodiment 1)

Figure 1:
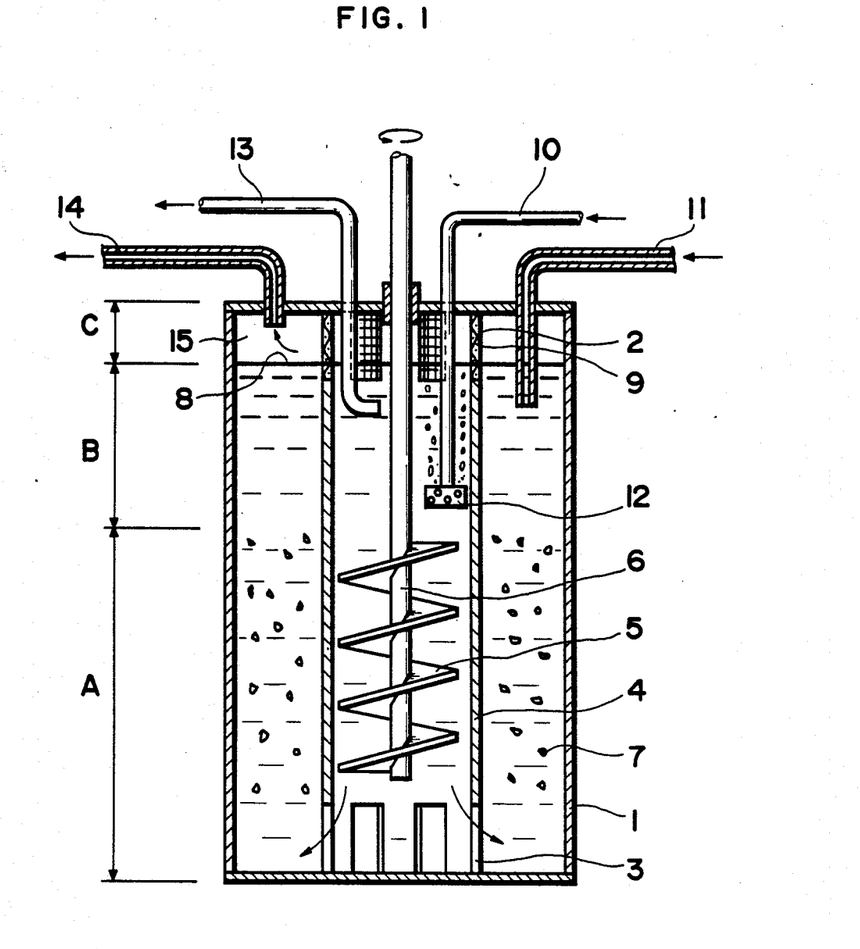
FIGS. 1 and 2 are sectional and perspective views, respectively, showing a first embodiment of the cell culture tank constructed in accordance with the present invention.
Figure 2:
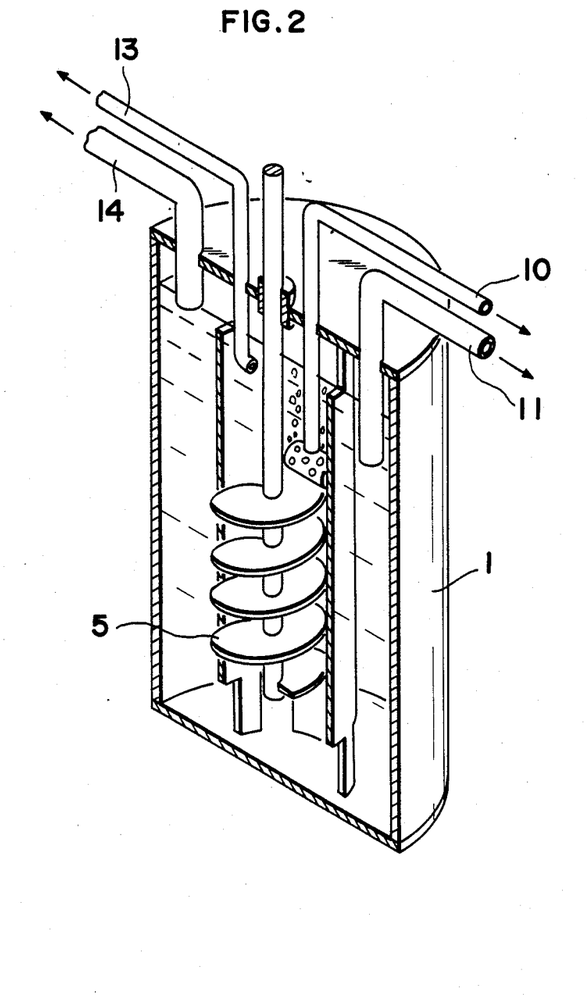

Referring to FIGS. 1 and 2, a cylindrical screen 4 having upper and lower openings 2, 3 is mounted upright within a cell culture tank 1. The opening 2 is provided with a filter 9 therein adapted to pass culture medium therethrough but to block adherent carriers while the opening 3 is grid-like and only the culture medium flows therethrough. As the filter 9 provided in the opening 2, a wide-meshed filter preferably made of material which is not gas-absorptive, e.g., glass, sintered metal, ceramics, paper, plastics and stainless meshes is used.

Said filter 9 may also be film such as ultrafiltration film adapted to pass compounds of relatively low molecular weights, for example, nutrient, or waste product or metabolism product from cells but to block compounds of relatively high molecular weights (e.g., 1,000 or higher, preferably 5,000 or higher).

An agitator 6 including a screw vane 5 is rotated within the cylindrical screen 4 to develop a downward flow of the culture medium.

The culture tank 1 is filled up to a liquid level 8 with the culture medium so that a space defined between the cylindrical screen 4 and the inner wall of the culture tank 1 may be filled up to a level sufficiently high to provide a floating region "A" within which the adherent carriers 7 float in the culture medium and a separating region "B" within which the adherent carriers are separated from the culture medium.

In the cell culture tank of the present invention, target cells are cultivated while they float in the culture medium. The culture medium is composed of aqueous medium, substantially being water, added with various additive ingredients conventionally used for the cell culture, for example, various types of inorganic salt, vitamin, coenzyme, glucose, amino acid and antibody. The culture medium may also contain serum and it is also possible to use as the culture medium so-called chemically defined medium which contains no serum.

There is provided within the cylindrical screen 4 an oxygen supply pipe 10 for supply of oxygen or oxygen containing gas and this pipe 10 supplies oxygen or oxygen containing gas through a nozzle 12 mounted on a forward end of the pipe into the culture medium.

Above the liquid level 8 of the culture tank 1, there is formed a gaseous region 15 and there are provided also above the liquid level 8 an inlet 11 and an outlet 13 for circulation of the culture medium. The forward end of the outlet 13 opens above the screw vane 5 provided within the cylindrical screen 4.

It should be noted that the medium outlet 13 requires no filter mounted on the forward end thereof when said outlet 13 opens within the cylindrical screen but requires such filter when the outlet 13 otherwise opens.

The medium inlet 11 shown has no filter on its forward end.

While there are separately provided the medium outlet 13 and the medium inlet 11 according to this embodiment, the medium inlet and the medium outlet may be implemented as a single circulating pipe.

Reference numeral 14 designates a gas exhaust pipe adapted to exhaust cell metabolism gas from the gaseous region "C" formed as a result of oxygen supply between the liquid level 8 and the top wall of the culture tank 1 to the exterior.

There is provided within the exhaust pipe a filter for filtration of contaminating bacteria.

A manner in which the first embodiment operates will be explained.

Oxygen is supplied through the nozzle 12 on the forward end of the oxygen supply pipe 10 into the culture medium and dissolved therein, and then a quantity of oxygen which has not been dissolved in the culture medium is exhausted together with the cell metabolism gas from the gaseous region "C" defined above the liquid level 8 of the culture medium through the exhaust pipe 14 to the exterior. The culture medium now containing an adequate quantity of oxygen dissolved therein is driven by the agitator 6 to flow downward through the lower opening 3 of the cylindrical screen 4 and then to flow upward into the region "A" defined between the cylindrical screen 4 and the inner wall of the culture tank 1.

The adherent carriers 7 float upward as the culture medium flows upward, but, when a predetermined level is reached, a sinking velocity of the adherent carriers exceeds an ascending velocity of the culture medium, resulting in that the adherent carriers are dynamically separated from the culture medium and only the latter flows through the upper opening 2 of the cylindrical screen 4 thereinto.

Thus, the adherent carriers for the target cells remain within the floating region "A" and continue their contribution to the cell culture.

In this way, supply of oxygen or oxygen containing gas into the culture medium occurs within the cylindrical screen 4 through the nozzle 12 located above the agitator vane 5, namely, into the quantity of culture medium containing therein no adherent carriers 7, so the cells are conveniently free from any mechanical damage by a shearing force developed due to a turbulent flow produced as oxygen is supplied into the culture medium.

The medium outlet 13 for circulation opens within the cylindrical screen 4 and, therefore, no filter is necessary to prevent the adherent carriers from flowing out. Such arrangement that no filter is provided on the forward end of the medium outlet 13 is advantageous in that the culture medium can be circulated without bothering about clogging of the filter with the adherent carriers.

It should be understood that, in FIG. 2, the cell culture tank is shown as having the filter being removed, and that the adherent carriers 7 may be those using microcapsules.

(Embodiment 2)

Figure 3:
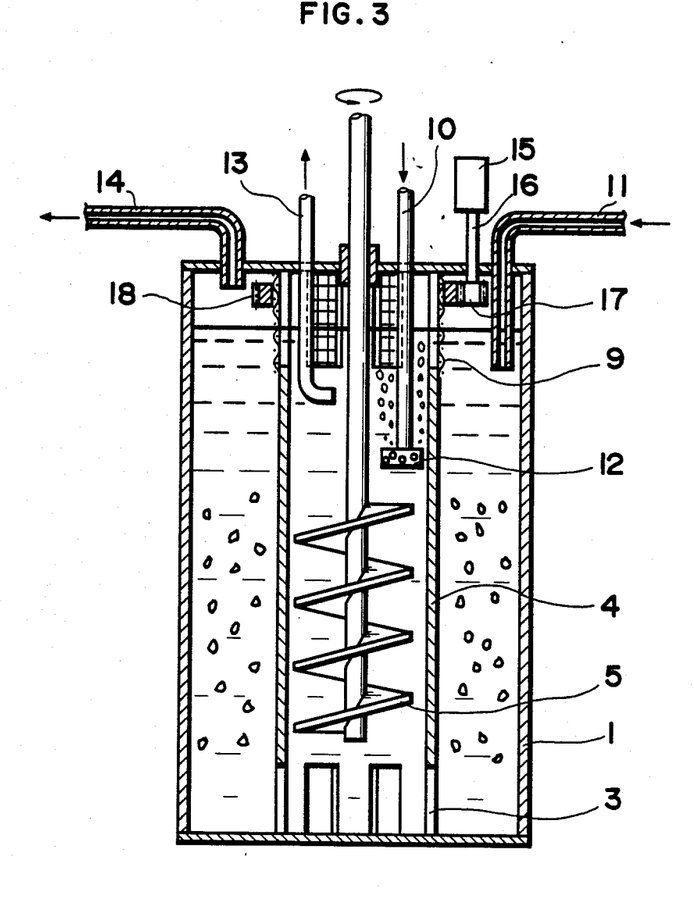
FIG. 3 is a sectional view showing a second embodiment of the present invention, in which the filter is rotatable.

FIG. 3 shows the second embodiment of the present invention, in which the filter is rotatable within the cell culture tank. Specifically, there is provided within the culture tank 1 around the upper opening 2 of the cylindrical screen 4 a cylindrical filter 9 adapted to pass the culture medium therethrough but to block the adherent carriers 7. The culture tank 1 is provided at its upper portion with an electromotor 15 of which a drive shaft 16 is provided, in turn, on its lower end with a pinion gear 17 adapted to be engaged with a ring gear 18 mounted around the filter 9, so that the electromotor 15 rotatably drives the filter 9.

It is also contemplated that the means to rotate the filter 9 utilizes a driving force provided from the electromotor for the agitator vane 5.

While such arrangement increases a possibility that the adherent carriers may adhere to the filter, this adhesion force is very weak and the adherent carriers are easily released from the filter as the latter is rotated.

(Embodiment 3)

Figure 4:
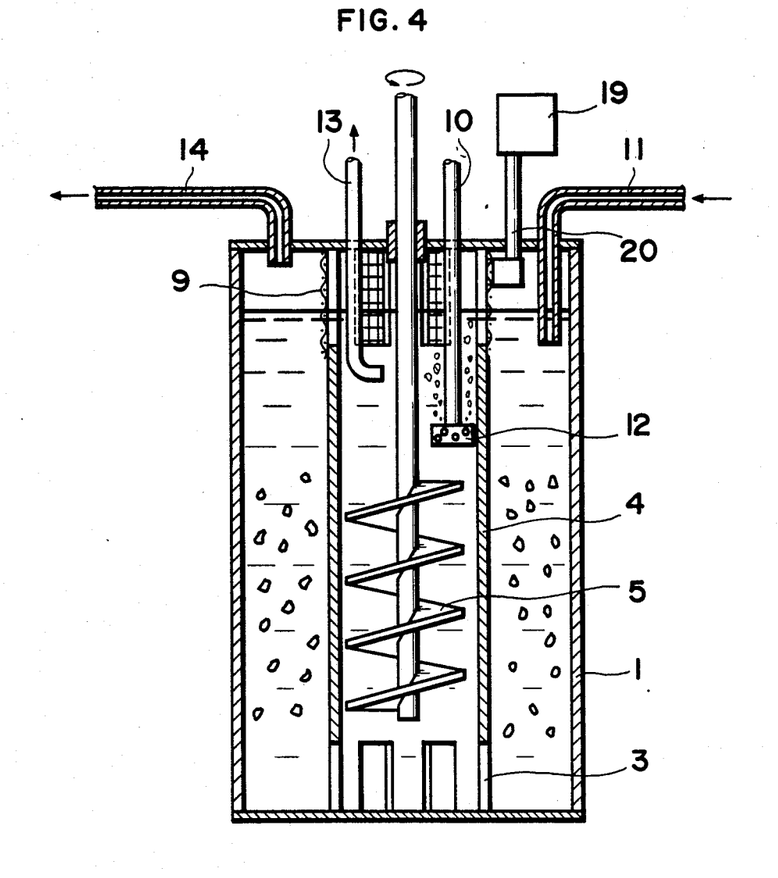
FIG. 4 is a sectional view showing a third embodiment of the present invention, in which the filter is vibrated.

FIG. 4 shows the third embodiment of the present invention, in which the filter 9 is intentionally vibrated.

The purpose of vibrating the filter is same just as the purpose of rotating the filter in the second embodiment, namely, to release the adherent carriers from the filter. To this end, the culture tank 1 is provided at its upper portion with a mechanical or electrical oscillator 19 having an actuator lever 20 of which a lower end bears against the filter so that the oscillator 19 may vibrate the filter 9.

(Embodiment 4)

Figure 5:
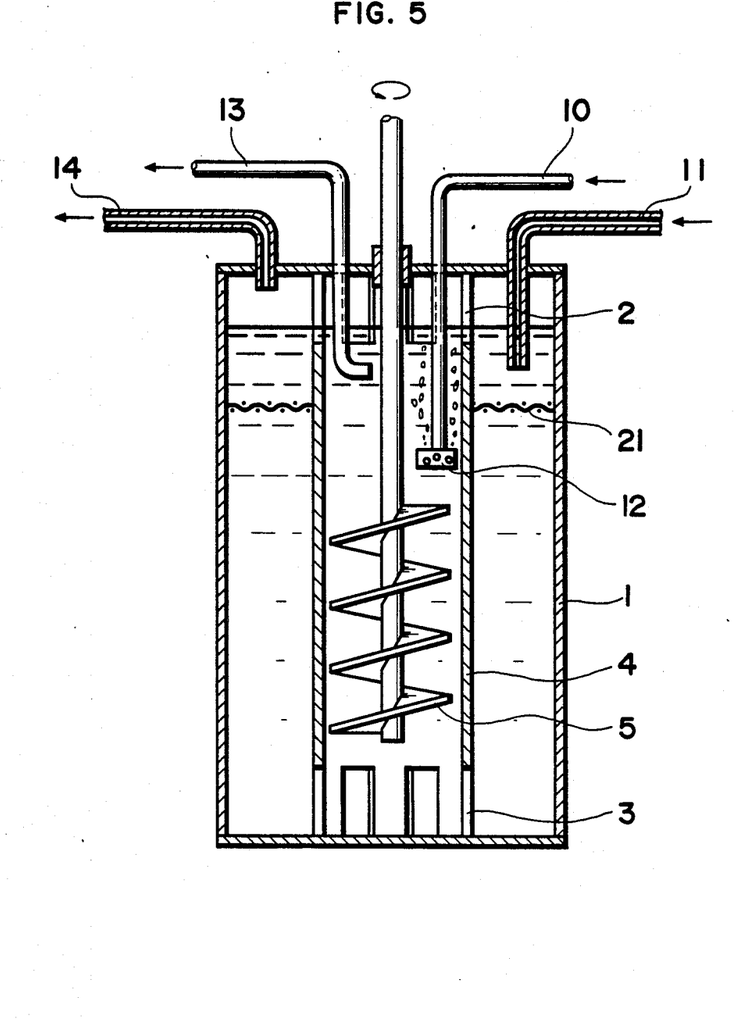
FIG. 5 is a sectional view showing a fourth embodiment of the present invention in which there is provided a disc-like filter between the cylindrical screen and the inner wall of the culture tank.

FIG. 5 shows the fourth embodiment of the present invention, in which there is provided between the cylindrical screen 4 and the inner wall of the culture tank 1 a disc-like filter 21. In this embodiment, the floating area A within which the adherent carriers 7 float in the culture medium and the separating region B within which the adherent carriers 7 are separated from the culture medium are implemented as separate devices.

(Embodiment 5)

Figure 7:
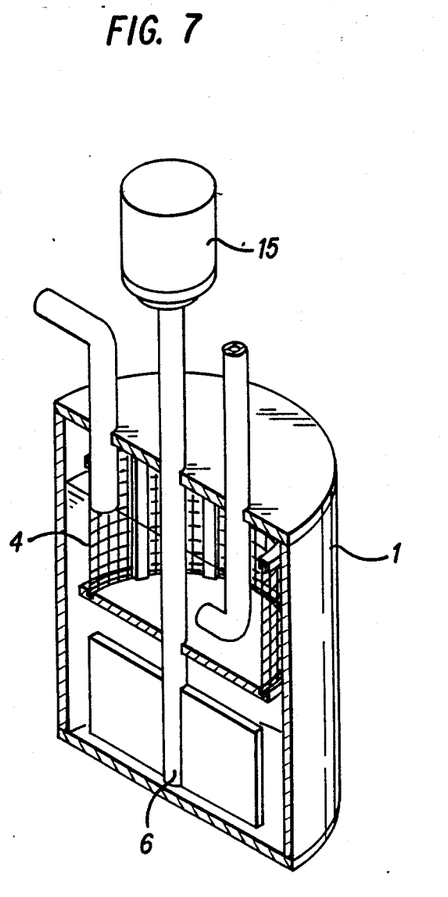
FIG. 7 is a perspective, partially sectioned, view of a further embodiment of the invention.

In accordance with a fifth embodiment of the present invention, which is shown in FIG. 7 of the accompanying drawings this embodiment is substantially the same as the embodiments previously discussed and shown in the drawings, except as follows. In this embodiment, the agitator 6 is coupled to the cylindrical screen 4 so as to rotate the cylindrical screen 4 by motor 15 together with the agitator 6 and thereby a rotating flow is developed in addition to the ascending flow in the culture medium around the cylindrical screen for further effective agitation.

As will be apparent from the foregoing description, the present invention, when applied to the cell culture tank, achieves the high density cell culture by supplying an adequate quantity of oxygen to be consumed by the target cells without any damage to the cells.

While the invention has been particularly shown and described with reference to preferred embodiments thereof, it will be understood by those skilled in the art that the foregoing and other changes in form and details can be made therein without departing from the spirit and scope of the invention.

What is claimed is:

1. A cell culture tank for culturing a culture medium having adherent carriers, comprising a cylindrical screen mounted upright within a cell culture tank and having upper and lower openings through which culture medium flows, said upper opening of the cylindrical screen being provided with a rotatable cylindrical filter adapted to pass the culture medium therethrough but to block the adherent carriers, a pipe for supply of oxygen or oxygen containing gas and an agitator adapted to produce a flow of the culture medium, and wherein both said pipe and said agitator are disposed within said cylindrical screen, so that a space defined between the cylindrical screen and the inner wall of the cell culture tank vertically consists of a floating region within which adherent carriers float in the culture medium and a separating region within which said adherent carriers are separated from the culture medium.

2. A cell culture tank for culturing a culture medium having adherent carriers, comprising a cylindrical screen mounted upright within a cell culture tank and having upper and lower openings through which culture medium flows, a disc-like filter disposed between the cylindrical screen and the inner wall of the cell culture tank and adapted to pass the culture medium therethrough but to block the adherent carriers, a pipe for supply or oxygen or oxygen containing gas and an agitator adapted to produce a flow of the culture medium, and wherein both said pipe and said agitator are disposed within said cylindrical screen, so that a space defined between the cylindrical screen and the inner wall of the cell culture tank vertically consists of a floating region within which adherent carriers float in the culture medium and a separating region within which said adherent carriers are separated from the culture medium.

3. A cell culture tank as recited in claim 2, wherein said disc-like filter is rotatable.

4. A cell culture tank as recited in claim 2, wherein said disc-like filter is vibratable by an oscillator.

5. A cell culture tank for culturing a culture medium having adherent carriers, comprising a cylindrical screen mounted upright within a cell culture tank and having upper and lower openings through which culture medium flows, said upper opening of the cylindrical screen being provided with a cylindrical filter which is vibratable by an oscillator and adapted to pass the culture medium therethrough but to block the adherent carriers, a pipe for supply of oxygen or oxygen containing gas and an agitator adapted to produce a flow of the culture medium, and wherein both said pipe and said agitator are disposed within said cylindrical screen, so that a space defined between the cylindrical screen and the inner wall of the cell culture tank vertically consists of a floating region within which adherent carriers float in the culture medium and a separating region within which said adherent carriers are separated from the culture medium.

6. A cell culture tank for culturing a culture medium having adherent carriers, comprising a cylindrical screen mounted upright within a cell culture tank and having upper and lower openings through which culture medium flows, a pipe for supply of oxygen or oxygen containing gas and an agitator adapted to produce a flow of the culture medium, said cylindrical screen being coupled to the agitator so as to rotate the cylindrical screen together with the agitator, and wherein both said pipe and said agitator are disposed within said cylindrical screen, so that a space defined between the cylindrical screen and the inner wall of the cell culture tank vertically consists of a floating region within which adherent carriers float in the culture medium and a separating region within which said adherent carriers are separated from the culture medium.

7. A cell culture tank as recited in any one of claims 3, 4, 2, 5 and 6, wherein a circulating pipe is provided within the cylindrical screen to circulate the culture medium.

8. A cell culture tank as recited in any one of claims 3, 4, 1, 2, 5 and 6, wherein the agitator comprises a helical vane.

* * * * *